US00PP24963P3

(12) United States Plant Patent
Thibault

(10) Patent No.: US PP24,963 P3
(45) Date of Patent: Oct. 14, 2014

(54) PEAR TREE NAMED 'CEPUNA'

(50) Latin Name: *Pyrus communis L.*
Varietal Denomination: Cepuna

(71) Applicant: Institute National de la Recherche Agronomique, Beaucouze (FR)

(72) Inventor: Bernard Thibault, Beaucouze (FR)

(73) Assignee: Institut National de la Recherche Agronomique, Beaucouze (FR)

( * ) Notice: Subject to any disclaimer, the term of this patent is extended or adjusted under 35 U.S.C. 154(b) by 161 days.

(21) Appl. No.: 13/573,999

(22) Filed: Oct. 18, 2012

(65) Prior Publication Data

US 2014/0115742 P1 Apr. 24, 2014

(51) Int. Cl.
*A01H 5/00* (2006.01)

(52) U.S. Cl.
USPC ..... Plt./188

(58) Field of Classification Search
USPC ..... Plt./188
See application file for complete search history.

*Primary Examiner* — Wendy C Haas
(74) *Attorney, Agent, or Firm* — Michelle Bos

(57) ABSTRACT

'Cepuna' pear tree is characterized by its productive bearing and attractive non-russeting fruit.

8 Drawing Sheets

Latin name: *Pyrus communis* L.
Variety denomination: 'Cepuna'.

BACKGROUND OF THE VARIETY

'Cepuna' is a new and distinct cultivar of pear tree *Pyrus communis* L. This new cultivar is a product of a controlled cross made in 1963 Angers, France of female parent 'Conférence' (not patented)×male parent 'Doyenné d'Hiver' (not patented). The variety was asexually reproduced by budding in 1974 at Angers and has been observed to remain true to type over successive asexually propagated generations.

BRIEF DESCRIPTION OF THE VARIETY

'Cepuna' pear tree is characterized by its productive bearing and attractive non-russeting fruit. It is distinguished from female parent 'Conférence' by its fruit, which exhibits less russeting. The concave profile of the fruit of 'Cepuna' distinguishes the variety from male parent 'Doyenné d'Hiver,' which bears globose fruit.

BRIEF DESCRIPTION OF THE PHOTOGRAPHS

Figure 1:
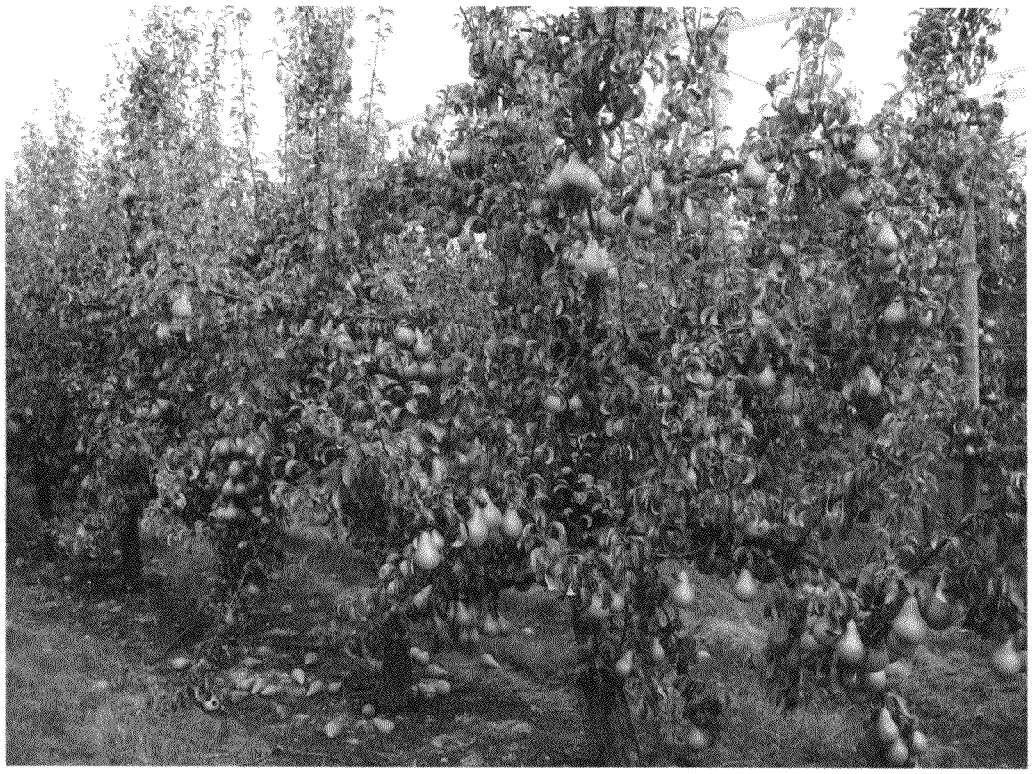
Figure 2:
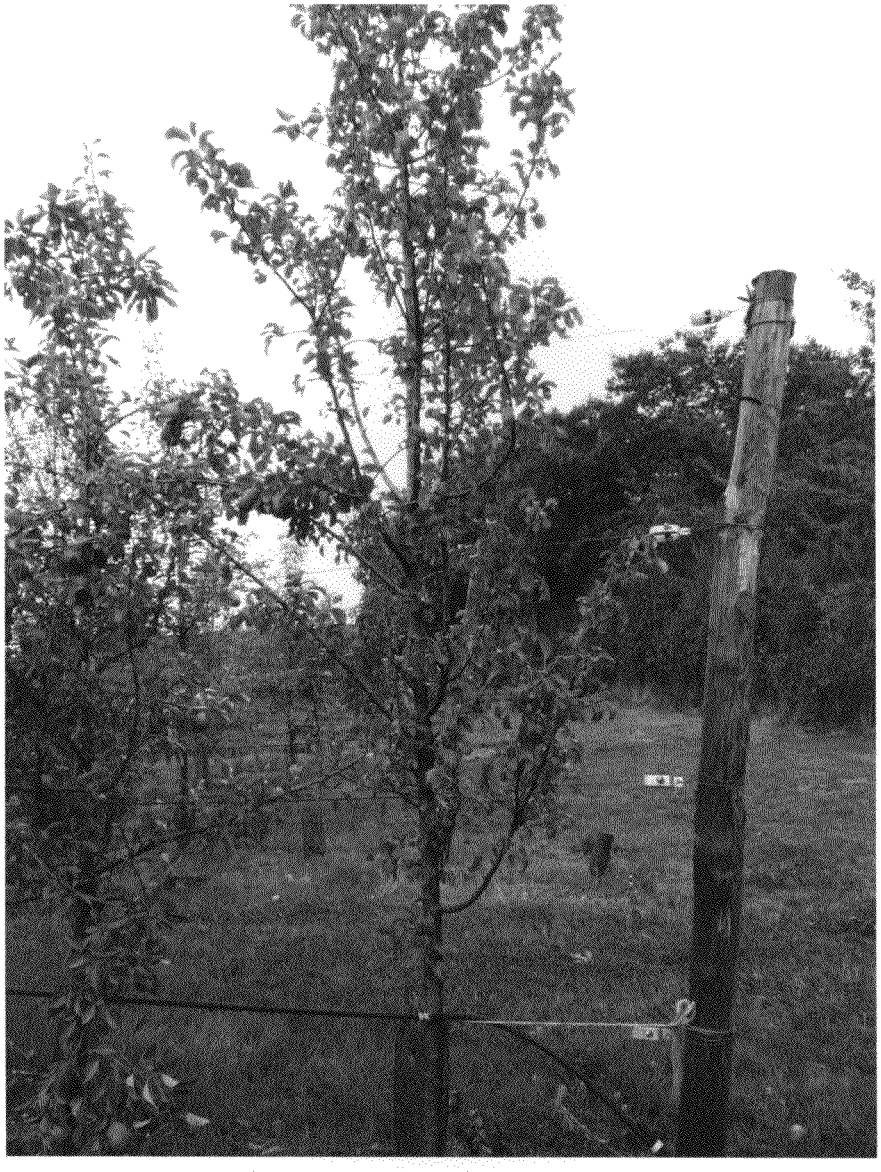
Figure 3:
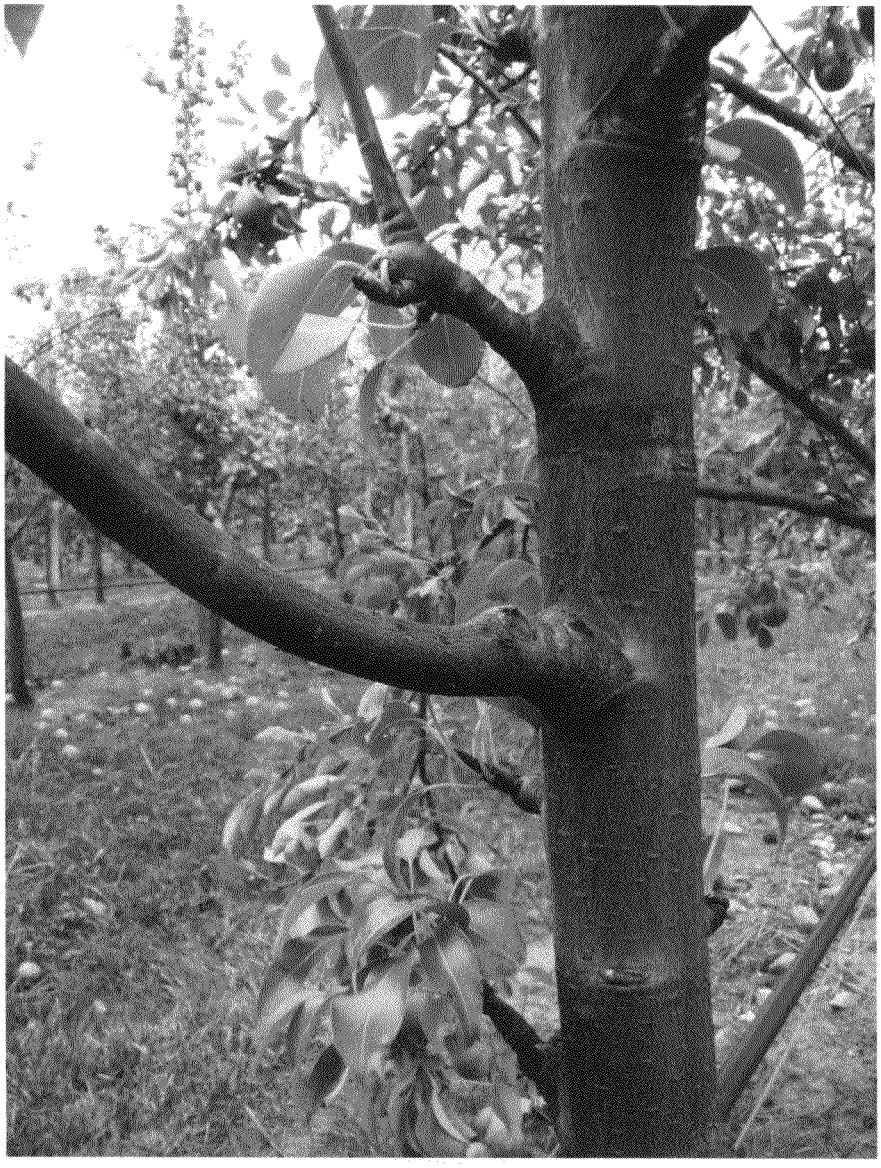
Figure 4:
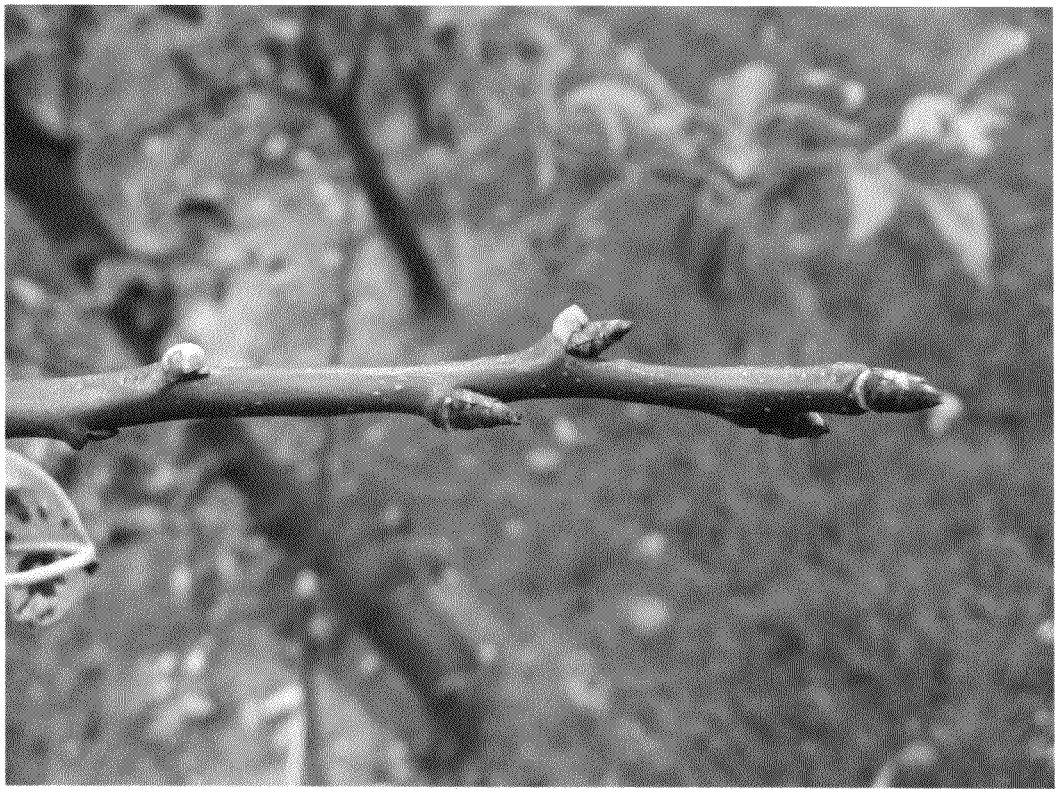
Figure 5:
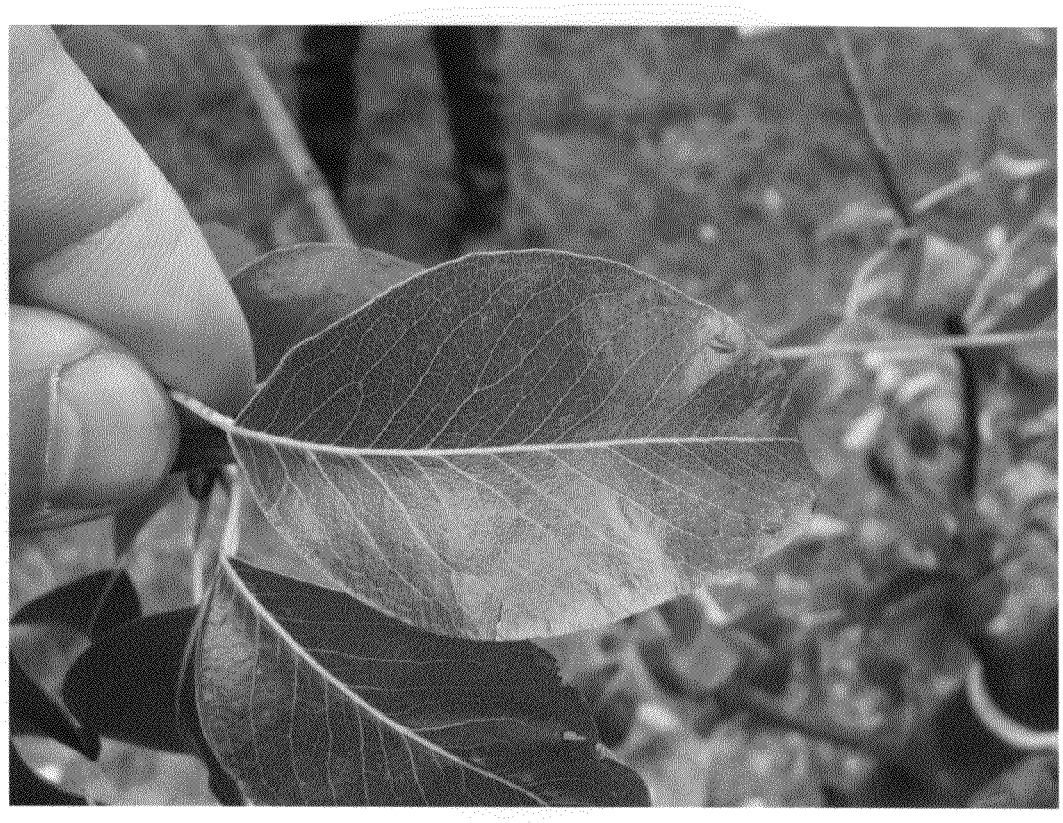
Figure 6:
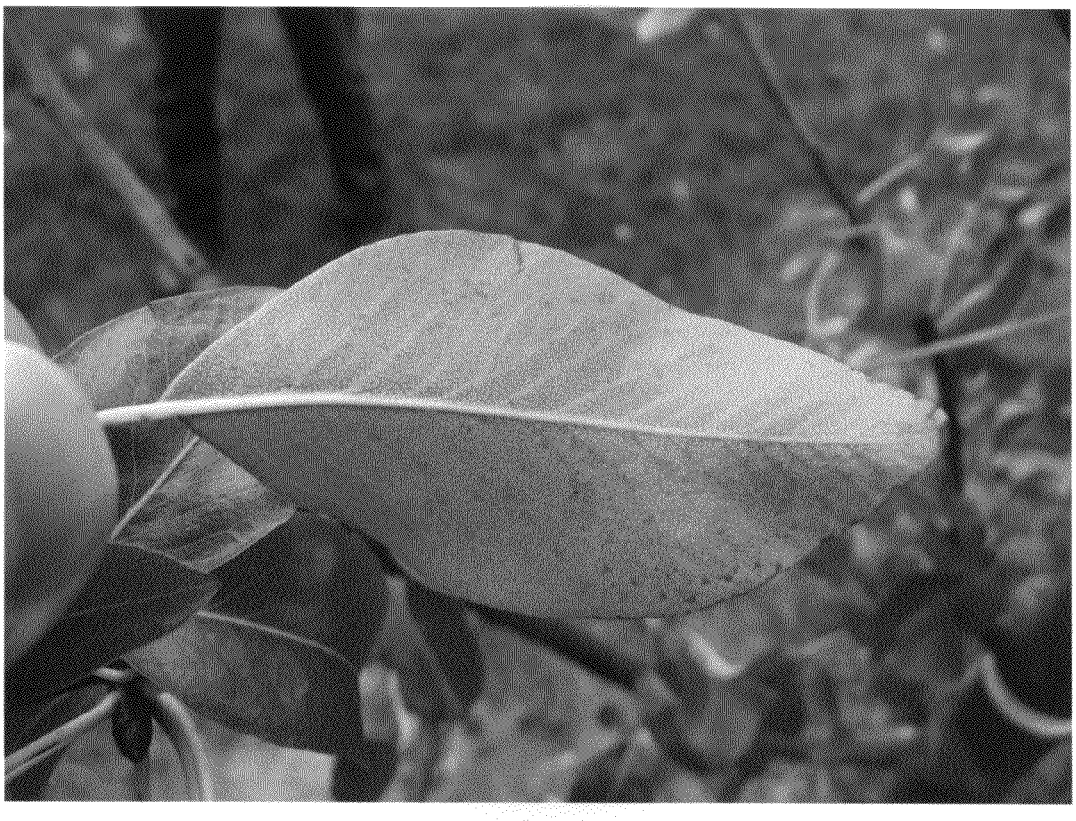
Figure 7:
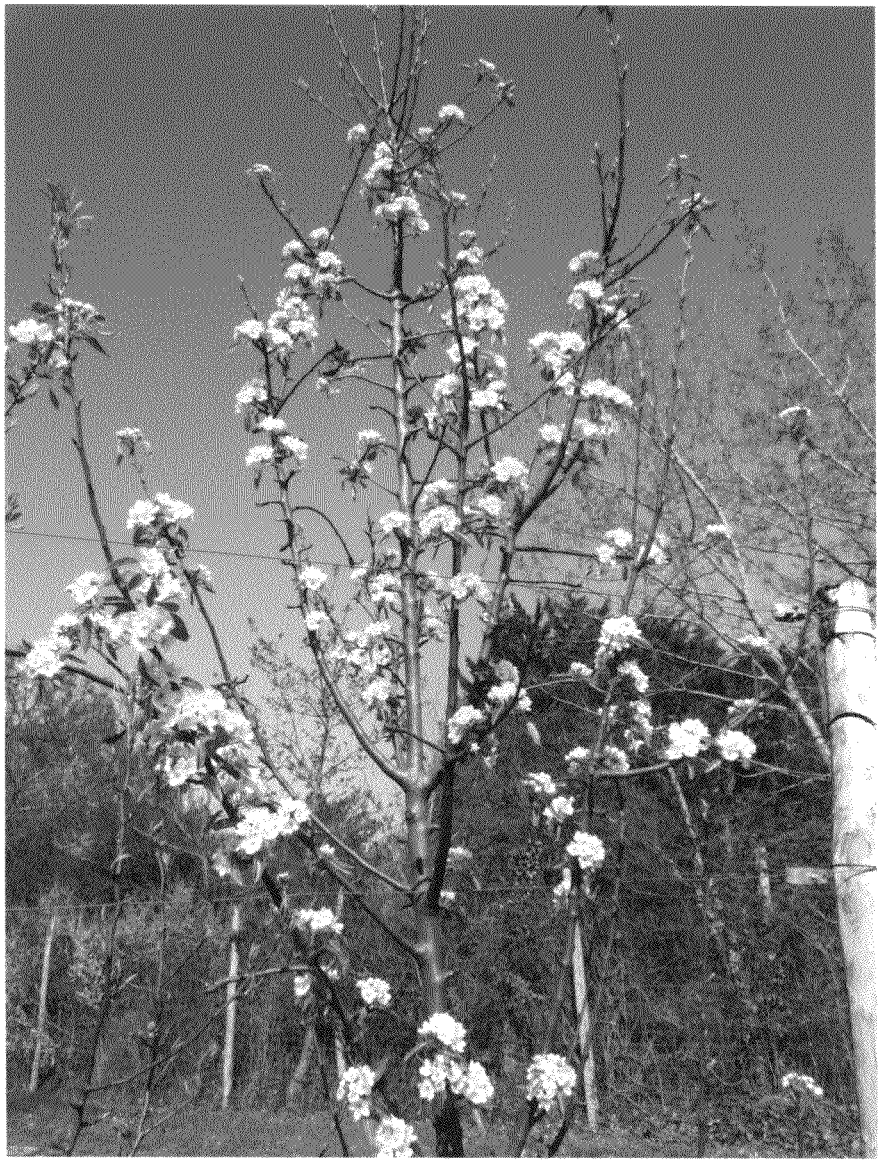
Figure 8:
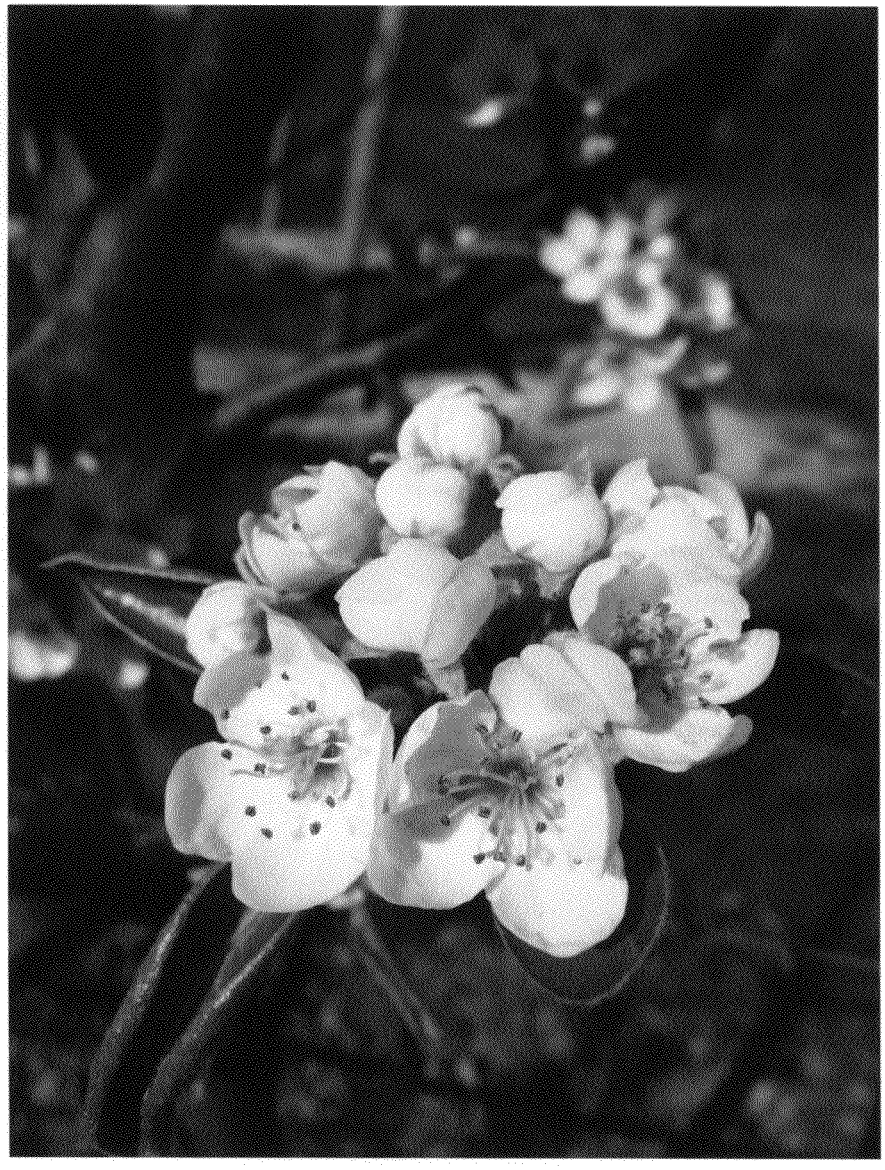

FIG. 1 shows the tree and fruit of the new variety;
FIG. 2 shows a tree of the new variety;
FIG. 3 shows the trunk and branch of the new variety;
FIG. 4 shows a one year old shoot of the new variety;
FIG. 5 shows the upper surface of a leaf of the new variety;
FIG. 6 shows the lower surface of a leaf of the new variety;
FIG. 7 shows the tree and blossoms of the new variety; and
FIG. 8 shows the blossoms of the new variety.

DETAILED BOTANICAL DESCRIPTION OF THE VARIETY

The following-detailed botanical description is based on observations made during the 2012 growing season at Beaucouze, France, of trees planted in 2007 on 'BA29' rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

DETAILED BOTANICAL DESCRIPTION

Tree:
- *Vigor*.—Average.
- *Type*.—Semi-erect.
- *Height*.—3.50 m.
- *Spread*.—1.3 m.
- *Trunk diameter* (*at* 30 *cm above the graft*).—70 mm.
- *Bark texture*.—Rough.
- *Winter hardiness*.—Good.

Branch (fruiting branches located at around 1 m above the graft union):
- *Length*.—1.60 m.
- *Diameter*.—35 mm.
- *Crotch angle*.—40°.
- *Bark color*.—Greyed-orange 177C.

One year old shoot:
- *Length*.—60 cm.
- *Color*.—Greyed-orange 175B.
- *Pubescence*.—None.
- *Thickness*.—6.0 mm.
- *Internode length*.—3 cm.
- *Number of lenticels*.—6 to 8/cm$^2$.
- *Vegetative bud shape*.—Acute.
- *Vegetative bud color*.—Greyed-purple 183A.
- *Position of vegetative buds in relation to shoot*.—Markedly held out.

Flowers:
- *Diameter of fully open flower*.—30 to 35 mm.
- *Depth of open flower*.—10 mm.
- *Relative position of petal margin*.—Touching.

*Number per cluster.*—12 to 14.
*Date of first bloom.*—31 Mar. 2012.
*Date of full bloom.*—4 Apr. 2012.
*Pollination requirement.*—Pollinator required.

Petals:
*Number per flower.*—5.
*Shape.*—Round.
*Length.*—15 mm.
*Width.*—12 mm.
*Margin.*—Smooth.
*Coloration of upper surface.*—Pink 56D.
*Coloration of lower surface.*—White 155D.

Pistils:
*Size.*—8 mm.
*Color.*—Yellow-green 145C.

Stigma:
*Size.*—0.6 mm.
*Color.*—Greyed-yellow 160A.

Style:
*Length.*—7 mm.
*Color.*—Yellow-green 145C.

Ovary:
*Size.*—5 mm.
*Color.*—Yellow-green 144C.

Anthers:
*Quantity.*—18 to 22.
*Length.*—1.5 mm.
*Presence of pollen.*—Yes.
*Color of pollen.*—Pink 49C.

Pedicel:
*Length.*—12 to 16 mm.
*Diameter.*—1.5 mm.
*Color.*—Yellow-green 144C.

Sepals:
*Quantity.*—5.
*Color.*—Yellow-green 144C.
*Length.*—6 mm.
*Width.*—4 mm.

Leaves:
*Shape.*—Oblong.
*Length.*—8.5.
*Width.*—4.0.
*Length/width ratio.*—2.12.
*Color of upper surface.*—Green 143B.
*Color of lower surface.*—Yellow-green 145A.
*Attitude in relation to shoot.*—Medium.
*Curvature of longitudinal axis.*—Medium.

Petiole:
*Length.*—3 cm.
*Diameter.*—1.5 mm.
*Coloration.*—Yellow-green 151A.
*Stipule color.*—Yellow-green 144B.
*Stipule shape.*—Elongated.
*Stipule length.*—5.5 cm.
*Stipule width.*—1.7 mm.

Fruit:
*Quantity per cluster.*—1 to 2.
*Height.*—100 mm.
*Width.*—70 mm.
*Ratio of height to width.*—1.42.
*Weight.*—220 g.
*Position of maximum diameter.*—Slightly toward the calyx.
*Symmetry in longitudinal section.*—Symmetrical.
*Profile of sides.*—Slightly concave.
*Skin texture.*—Smooth.
*Background color of skin.*—Yellow-green.
*Area of over color of skin.*—Absent or very small.
*Color of overcolor.*—Pink red.
*Relative area of russet around eye basis.*—Absent or very small.
*Relative area of russet on cheeks.*—Absent or very small.
*Relative area of russet on stalk attachment.*—Absent or very small.
*Length of stalk.*—Medium.
*Thickness of stalk.*—Thin.
*Curvature of stalk.*—Absent or very weak.
*Attitude of stalk in relation to axis of fruit.*—Straight.
*Stalk color.*—Greyed-orange 175A.
*Depth of eye basin.*—Shallow.
*Width of eye basin.*—Narrow.
*Attitude of sepals at harvest.*—Converging.
*Firmness of flesh.*—Medium.
*Flesh texture.*—Medium fine.
*Aroma.*—Light aroma.
*Juiciness.*—Medium.
*Brix.*—13.0° to 14.5°.

Seeds:
*Quantity per fruit.*—7.
*Shape.*—Elliptic.
*Length.*—Medium.
*Width.*—Medium.

Harvest:
*Time for harvest.*—First week of September.
*Time of maturity for consumption.*—October to February.
*Amount of fruit produced per tree per harvest.*—30 kg.

Disease resistance/susceptibility: Medium sensibility for fire blight ISV 42.

Market use: Fresh fruit.

Storage characteristics: Very good storage.

The invention claimed is:

1. I claim a new and distinct pear tree substantially as described and illustrated herein.

* * * * *